United States Patent
Cahoon et al.

(10) Patent No.: US 6,900,041 B2
(45) Date of Patent: May 31, 2005

(54) METHODS AND COMPOSITIONS FOR THE TREATMENT OF INFLAMMATORY DISEASES

(75) Inventors: Shianlen Cahoon, Atlanta, GA (US); Sivaram Pillarisetti, Norcross, GA (US); Uday Saxena, Atlanta, GA (US); Angela Vines, Atlanta, GA (US)

(73) Assignee: Reddy US Therapeutics Inc., Norcross, GA (US)

( * ) Notice: Subject to any disclaimer, the term of this patent is extended or adjusted under 35 U.S.C. 154(b) by 69 days.

(21) Appl. No.: 09/969,013

(22) Filed: Oct. 2, 2001

(65) Prior Publication Data

US 2002/0077293 A1 Jun. 20, 2002

Related U.S. Application Data

(60) Provisional application No. 60/237,147, filed on Oct. 2, 2000.

(51) Int. Cl.[7] .......................... C12N 9/12; G01N 33/53
(52) U.S. Cl. ....................... 435/194; 435/7.1; 435/183; 435/320.1; 435/325; 424/85.1; 514/12; 530/350; 536/23.1
(58) Field of Search ........................ 435/7.1, 183, 194, 435/320.1, 325; 424/85.1; 514/12; 530/350; 536/23.1

(56) References Cited

U.S. PATENT DOCUMENTS 6,479,490 B2 * 11/2002 Gong et al. ............... 514/235.5
2002/0086282 A1 * 7/2002 Phullarisetti et al. .......... 435/4

OTHER PUBLICATIONS

Badrichani, A.Z., et al., "Bcl–2 and Bcl–$X_L$ Serve an Anti–Inflammatory Function in Endothelial Cells Through Inhibition of NF–κB", The Journal of Clinical Investigation, vol. 103, No. 4: pp. 543–553 (1999).
Banba, Nobuyuki, et al., "Possible Relationship of Monocyte Chemoattrractant Protein–1 With Diabetic Nephropathy", Kidney International, vol. 58, No. 2: pp. 684–690 (2000).
Beg, Amer A, et al., "An Essential Rose for NF–κB in Preventing TNF–α–Induced Cell Death", Science, vol. 274: pp. 782–784 (1996).
Cross, Darren A.E., et al., "Inhibition of Glycogen Synthase Kinase–3 by Insulin Mediated by Protein Kinase B", Nature, vol. 378, No. 6559: pp. 785–789 (1995).
Fiol, Carol J., et al., "A Secondary Phosphorylation of CREB[341] at Ser[129] is Required for the cAMP–mediated Control of Gene Expression", The Journal of Biochemistry, vol. 269, No. 51: pp. 32187–32193 (1994).
Green, E. Allison, et al., "Tumor Necrosis Factor–α and the Progression Of Diabetes in Non–Obese Diabetic Mice", Immunological Reviews, vol. 169: pp. 11–22 (1999).
Hanger, Diane P., et al., "Glycogen Synthase Kinase–3 Induces Alzheimer's Disease–Like Phosphrylation of Tau: Generation of Paired Helical Filament Epitopes and Neuronal Localisation of the Kinase", Neuroscience Letters, vol. 147: pp. 58–62 (1992).
Kim, Leung, et al., "GSK3, a Master Switch Regulating Cell–Fate Specification and Tumorigenesis", Current Opinion in Genetics & Development, vol. 10, No. 5: pp. 508–514 (2000).
Klein, Peter S. et al., "A Molecular Mechanism for the Effect of Lithium on Development", Pro. Natl. Acad. Sci. USA, vol. 93, No. 15: pp. 8455–8459 (1996).
Laight, David W. et al., "Endothelial Cell Dysfunction and the Pathogenesis of Diabetic Macroangiopathy", Diabetes Metab. Res. Rev., vol. 15, No. 4: pp. 274–282 (1999).
Lau, K.F. et al., "Expression Analysis of Glycogen Synthase Kinase–3 in Human Tissues", J. Peptide Res., vol. 54, No. 1: pp. 85–91 (1999).
Lesort, Matheiu, et al., "Insulin Transietnly Increases Tau Phosphorylation: Involvement of Glycogen Synthase Kinase–3β and Fyn Tyrosine Kinase", Journal of Neurochemistry, vol. 72, No. 2: pp. 576–584 (1999).
Raj, M.D., Dominic S.C. et al., "Advanced Glycation End Products: A Nephrologist's Perspective", American Journal of Kidney Diseases, vol. 35, No. 3: pp. 365–380 (2000).
Read, Margaret A.. et al., "NF–κB and IκBα: An Inducible Regulatory System in Endothelial Activation", Journal of Experimental Medicine, vol. 179, Nos. 1–3: pp. 503–512 (1994).
Ross, Sarah H., et al., "Glycogen Synthase Kinase 3 Is an Insulin–Regulated C/EBPα Kinase", Molecular and Cellular Biology, vol. 19, No. 12: pp. 8433–8441 (1999).
Stambolic, Vuk, et al., "Lithium Inhibits Glycogen Synthase Kinase–3 Activity and Mimics Wingless Signalling in Intact Cells", Current Biology, vol. 6, No. 12: pp. 1664–1668 (1996).
Stehouwer, Coen D.A.., et al., "Endothelial Dysfunction and Pathogenesis of Diabetic Angiopathy", Cardiovascular Research, vol. 34: pp. 55–68 (1997).
Summers, Scott A., et al., "The Role of Glycogen Synthase Kinase 3β in Insulin–stimulated Glucose Metabolism", The Journal of Biological Chemistry, vol. 274, No. 25: pp. 17934–17940 (1999).

(Continued)

Primary Examiner—Jon Weber
Assistant Examiner—Chih-Min Kam
(74) Attorney, Agent, or Firm—Womble Carlyle Sandridge & Rice, PLLC

(57) ABSTRACT

The present invention is directed to compositions and methods for treating inflammatory diseases comprising administration of compositions that effect glycogen synthase kinase 3β (GSK-3β) protein or gene. The present invention also comprises methods and compositions for the identification of compounds or therapeutic agents which modulate the activity of the protein. The present invention provides compositions for and methods off treatment of biological conditions including, but not limited to, type I and type II diabetic induced vasculopathy, other vasculopathies, asthma and inflammation-induced diseases such as atherosclerosis and cell proliferation.

27 Claims, 11 Drawing Sheets

OTHER PUBLICATIONS

Sutherland, Calumn, et al., "Inactivation of Glycogen Synthase Kinase–3β by Phosphorylation: New Kinase Connections in Insulin and Growth–Factor Signalling", Biochemical Journal, vol. 296: pp. 15–19 (1993).

Tracey, Kevin J., et al. "Tumor Necrosis Factor, Other Cytokines and Disease", Annu. Rev. Cell Biol., vol. 9: pp. 317–343 (1993).

Van Antwerp, Daniel J., et al., "Suppression of TNFα – Induced Apoptosis by NF–κB", Science, vol. 274: pp. 787–789 (1996).

Welsh, Gavin, et al., "GSK3: a Shaggy Frog Story", Trends in Cell Biology, vol. 6: pp. 274–279 (1996).

Wilson, Byron E., et al., "Induction of blc–2 Expression by Phosphorylated CREB Proteins during B–Cell Activation and Rescue from Apoptosis", Molecular and Cellular Biology, vol. 16, No. 10: pp. 5546–5556 (1996).

* cited by examiner (a)

(b)

(a)

(b)

(c)
GSK-3β
Protein (a)

(b)

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 1
ttcctttgga atctgccatc                                          20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 2
gggtcggaag accttagtcc                                          20
```

```
<210> SEQ ID NO 3
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 3
atgtcagggc ggcccagaac cacctc                                          26

<210> SEQ ID NO 4
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 4
gaggtggttc tgggccgccc tgacat                                          26
```

Methods and Compositions for the Treatment of Inflammatory Diseases

RELATED APPLICATIONS

This application claims priority to U.S. Provisional Patent Application No. 60/237,147, filed Oct. 2, 2000, which is incorporated herein in its entirety.

TECHNICAL FIELD

The present invention relates to compositions and methods for treating chronic and acute inflammatory conditions. In particular, the present invention is directed to methods for detecting compounds that interact with the protein kinase, glycogen synthase kinase 3β (GSK-3β).

BACKGROUND OF THE INVENTION

Chronic and acute inflammatory conditions form the basis for diseases affecting all organ systems including, but not limited to, asthma, acute inflammatory diseases, vascular inflammatory disease, chronic inflammation, atherosclerosis, angiopathy, myocarditis, nephritis, Chron's disease, arthritis, type I and II diabetes and associated vascular pathologies. The incidence of these inflammatory conditions is on the rise in the population as a whole, with diabetes alone affecting 16 million people.

While inflammation in and of itself is a normal immune response, chronic inflammation leads to complications and ongoing system damage due to the interactions of unknown cellular factors. In particular, chronic inflammation can cause endothelial damage resulting in vascular complications. Coronary artery, cerbrovascular and peripheral vascular disease resulting from atherosclerotic and thromboembolic macroangiopathy are the primary causes of mortality in chronic inflammatory diseases. (1, 2)

Inflammation is maintained by inflammatory cytokines which increase production of growth promoting genes by vascular cells and leukocytes leading to increased lesion formation in blood vessels. IL-1, for example, increases the production of platelet derived growth factor A chain (PDGF) by smooth muscle cells. PDFG induces proliferation of fibroblasts, microglia, and smooth muscle. PDGF may also serve as a chemotactic agent for inflammatory cells, thereby continuing the cycle and leading to further damage.

Though currently there are pharmaceutical agents directed to treating inflammatory conditions, none of these agents are capable of specifically controlling cellular components triggered by inflammatory responses or components that are the triggering agent for inflammation. What is needed are compositions and methods that specifically target cellular components of inflammation to treat diseases and conditions that are caused by or lead to inflammatory states.

SUMMARY OF THE INVENTION

The present invention comprises compositions and methods for treating biological conditions, particularly inflammatory conditions such as, type I and type II diabetic induced vasculopathy, other vasculopathies, asthma and inflammation-induced diseases such as atherosclerosis and cellular proliferation.

In particular, a preferred embodiment of the present invention comprises methods and compositions for treating biological conditions mediated by GSK-3β. The present invention also comprises methods for identifying, making and using compositions that effect the activity of GSK-3β and the activity of biological molecules that effect the activity of GSK-3β. Preferred methods comprise administering an effective amount of a pharmaceutical composition comprising a selective activator of GSK-3β to a subject having an inflammatory-mediated condition or to a subject susceptible to such a condition. Such inflammatory-mediated conditions, or inflammatory diseases, include, but are not limited to, asthma, acute inflammation, chronic inflammation, type I diabetes or type II diabetes and all of the related pathologies. Other conditions that are treated by the compositions and methods of the present invention comprise precursors of inflammatory diseases or related conditions such as hyperinsulinemia.

The present invention further comprises the use of GSK-3β effectors in the treatment of proliferative disorders such as smooth muscle cell proliferation.

DETAILED DESCRIPTION OF THE INVENTION

Figure 1:
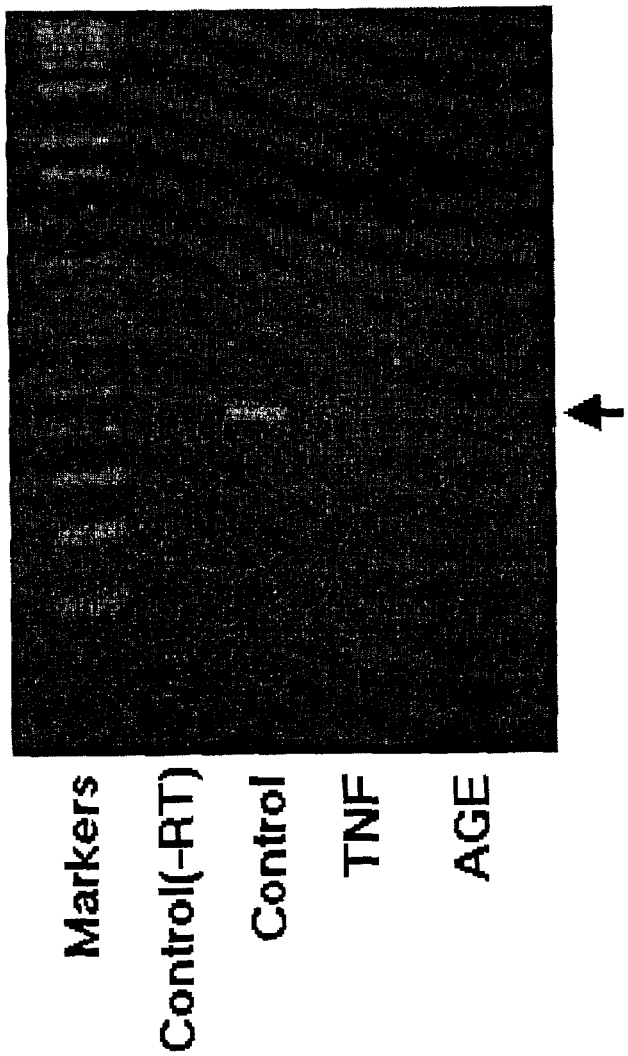
FIG. 1 is a picture of an electrophoreses gel showing the RT-PCR results in endothelial cells.

The present invention is directed to compositions and methods for the treatment of inflammatory disease states, preconditions and related conditions and pathologies. The present invention is also directed to assays and detection methods and compositions for determining compounds that effect cellular components involved in inflammatory disease states, preconditions and related conditions and pathologies. In particular, the present invention comprises preferred embodiments that are directed to methods and compositions that effect GSK-3β activity, most preferably, methods and compositions that up-regulate GSK-3β activity. The present invention is further directed to compositions and methods for controlling cell proliferation. In particular, the present invention comprises compositions that effect GSK-3β activity to promote cellular proliferation for the treatment of wounds, ulcers, and other conditions comprising regrowth of healthy tissue.

Glycogen synthase kinase 3 (GSK3) is a highly conserved protein kinase implicated in cell-fate determination and hormonal signaling. It was originally discovered as the kinase that phosphorylates glycogen synthase (1). GSK3 consists of two isoforms, α (GSK3α) and β (GSK-3β), which are ubiquitously expressed. GSK3 is constitutively active in resting cells, inhibiting glycogen synthase by direct phosphorylation. GSK3 preferentially phosphorylates serine and threonine residues in the amino acid motif serine-proline or threonine-proline. Since the original description of GSK3, other proteins have been identified that are phosphorylated or otherwise regulated by GSK-3β, including protein phosphatases, kinases, adhesion molecules, microtubule associated protein Tau, adenomatous polyposis coli gene product (APC) and several transcription factors including c-Jun/AP-1 and CCAAT/enhancer-binding protein (C/EBP) (3–6). Although transcriptional activators of GSK-3β have not yet been identified, the activity of GSK-3≈ can be regulated post-transcriptionally by phosphorylation (7–9). For example, the activity of GSK-3β can be down-regulated by direct phosphorylation of serine 9 which is catalyzed by the protein kinases such as p70S6K, p90rsk, certain isoforms of PKC (e.g. PKCδ), as well as the insulin-activated phosphatidyl inositol 3-kinase-PKB pathway (8, 9). Elevated levels of GSK-3β have been found in the skeletal muscle of diabetic patients, which may contribute to the impaired glycogen synthase activity and skeletal insulin resistance present in type II diabetes. Although GSK-3β is known to catalyze the phosphorylation of several protein kinases and other proteins, the specific role that GSK-3β has in cell signaling remains unclear. Mice with a disrupted GSK-3β gene develop liver degeneration during mid-gestation.

Though not wishing to be bound by any particular theory, it is believed that GSK-3β is required for NF-κB signaling and that GSK-3β promotes NF-κB -induced gene expression. NF-κB is a transcription factor that plays a necessary role in the activation of genes in response to inflammatory stimuli such as TNFα and interleukin –β (11, 12). Up-regulation of molecules involved in endothelial inflammation and leukocyte adhesion, such as vascular cell adhesion molecule-1 (VCAM-1), monocyte chemoattractant protein-1 (MCP-1), selecting, interferon-inducible protein (IP-10), monokine induced by IFN-g (MIG), interferon-inducible T-cell α chemoattractant (I-TAC), and interleukin-6, leads to endothelial dysfunction and vasculopathy (3, 4).

NF-κB is normally composed of two subunits, p50 and p65. In resting cells, NF-κB complexes are retained in the cytoplasm by association with an inhibitory protein termed I-κB. Activation of NF-κB requires the phosphorylation-dependent degradation of I-κB by the 26S proteosome. The free NF-κB dimer rapidly translocates to the nucleus and binds to NF-κB responsive sites, thereby exerting it's effect on gene expression. Early steps leading to NF-κB activation (degradation of I-κB and translocation of NF-κB to the nucleus) were unaffected by the loss of GSK-3β, indicating that NF-κB is regulated by GSK-3β after NF-κB translocation to the nucleus. However, an important conclusion to be drawn from this work is that only a subset of NF-κB-inducible genes are dependent upon GSK-3β function based on the observation that new I-κB synthesis, which is under the transcriptional control of NF-κB, is unchanged in GSK-3β-deficient cells.

The mechanism by which GSK-3β regulates NF-κB activity is unclear. Nonbinding theories include modulation, by phosphorylation, of the activities of transcription factors CCAAT/enhancer-binding protein (C/EBP) and cyclic AMP response element binding protein (CREB) (18, 19). GSK-3β can phosphorylate both C/EBP and CREB and positively regulate their activity. C/EBP are members of a family of basic region-leucine zipper transcription factors implicated in the regulation of pro-inflammatory cytokine expression as well as other gene products associated with macrophage activation and the acute-phase response. GSK-3β in conjunction with protein kinase A can phosphorylate CREB. Transfection of cells with GSK-3β induces a 60-fold increase in CREB-dependent transcription, mediated via the endogenous CREB protein (18). CREB regulates transcription of key endothelial survival genes such as bcl-2 (19). bcl-2 can in turn down regulate NF-κB resulting in decrease of inflammation (20).

In the literature, GSK-3β has been given several functions. These include inhibition of glycogen synthesis, modulation of glucose uptake by tissues and contribution to insulin resistance (5, 6, 21, 22). Recent data, however indicate that GSK-3β has little role, if at all in glucose/glycogen metabolism. Mice deficient in GSK-3β have normal glycogen metabolism and overexpression of GSK-3β in adipocytes did not significantly inhibit either Akt/PKB activity or insulin-stimulated glucose uptake. Thus GSK-3β is unlikely to contribute to insulin stimulation of glycogen synthesis nor glucose uptake or GLUT4 translocation.

Surprisingly, the present inventors have found that there is protective function for GSK-3β in opposing the NF-κB-induced inflammatory gene expression and that compositions and methods for increasing the GSK-3β activity are useful for treatment of inflammatory diseases, preconditions and related conditions and pathologies. Such pathologies include, but are not limited to, type I and type II diabetic induced vasculopathy, other vasculopathies such as nephropathy and retinopathy, asthma and atherosclerosis. For example, the present invention comprises compositions that effect GSK-3β regulation in tissues such as the kidney for treatment of local inflammatory response and nephropathy.

An aspect of the present invention comprises methods and compositions for the treatment of diseases, preconditions or pathologies associated with inflammatory cytokines including, but not limited to TNFα, IL-6, VCAM-1, AGE-induced MCP-1, selecting, IP-10, MIG and I-TAC. These cytokines are thought to effect the pathogenesis of atherosclerosis and the development of diabetic vasculopathy in type II diabetes. For example, affecting the activity or level of TNFα is a key mediator of tissue damage following acute or chronic inflammatory reactions. The present invention contemplates providing compositions and methods for up-regulating GSK-3β to counteract the effects of cytokines such as TNFα, IL-6, VCAM-1, IP-10, MIG, I-TAC and AGE-induced MCP-1, and treat the associated diseases, preconditions and pathologies.

For example, a preferred method comprises administering to a subject undergoing an acute inflammatory reaction, such as sepsis, an effective amount of a composition that causes an increase in the amount of GSK-3β protein or an increase in the level of activity of GSK-3β. Additionally, a preferred method comprises administering to a subject with a chronic inflammatory reaction, such as early stage diabetic vasculopathy, an effective amount of a composition that causes and maintains an increased amount of GSK-3β protein or an increased level of activity of GSK-3β that controls or stops the progression of the vasculopathy.

Figure 5:
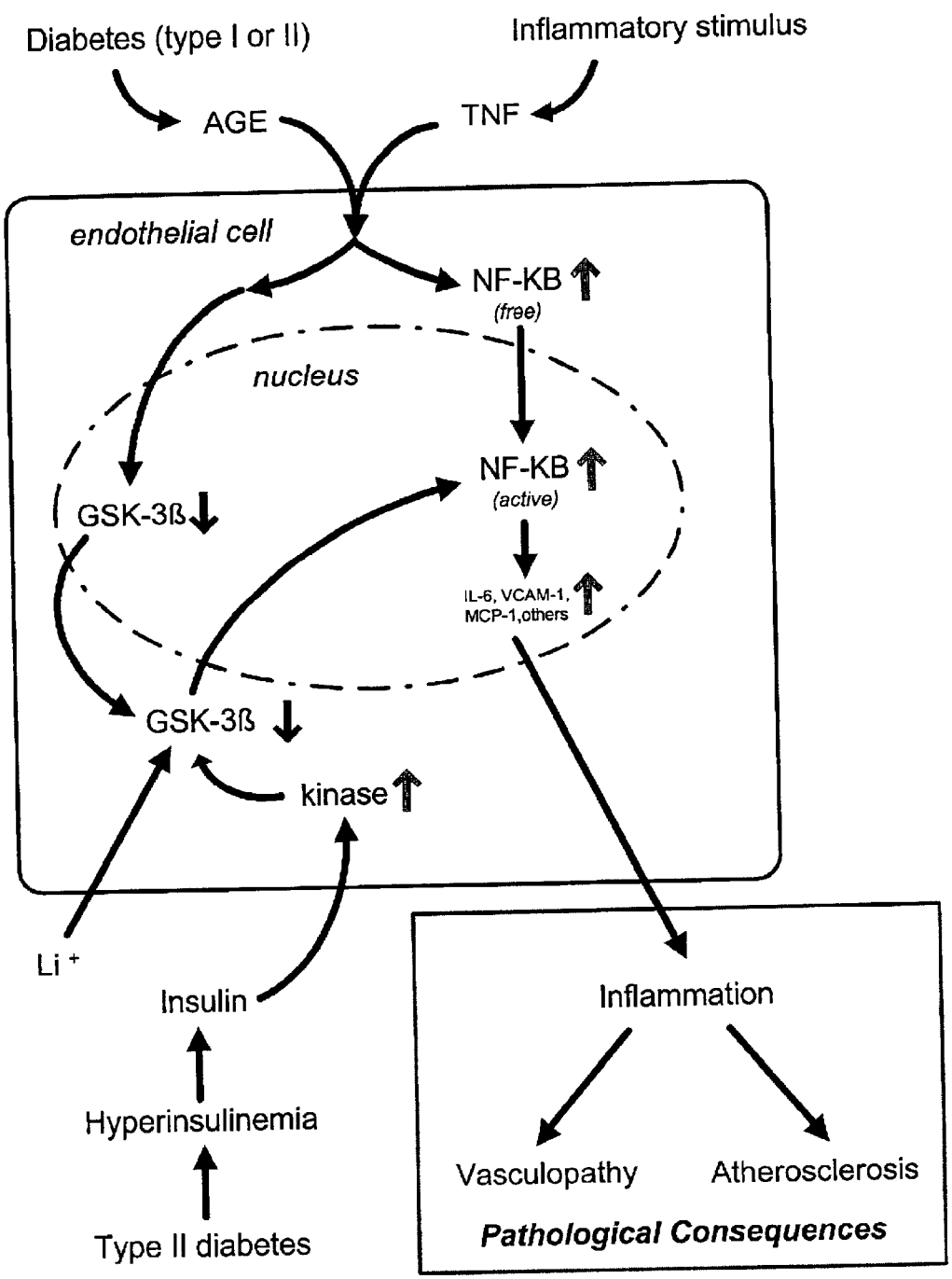
FIG. 5 is a schematic diagram illustrating several pathways that result in inhibition of GSK-3β production.

A preferred embodiment of the present invention comprises methods and compositions for the treatment of diabetic vasculopathy, such as that seen in type II diabetes. Type II diabetes is characterized by insulin resistance, hyperinsulinemia, and altered carbohydrate and lipid metabolism resulting in hyperglycemia and advanced glycation end product (AGE) formation. Though not wishing to be bound by any particular theory, it is theorized that the physiological conditions present in type II diabetes lead to negative regulation of GSK-3β by two independent pathways, one pathway activated by insulin and another pathway activated by AGE. AGE increases lipoprotein oxidizability and atherogenicity. AGE binding to matrix proteins induces synthesis of IL-1, TNFα, VCAM-1, Heme oxygenase, insulin like growth factor and IL-6, and activates NF-κB. It is believed that the down-regulation of GSK-3β by either or both pathways leads to severe vasculopathy (see FIG. 5). The currently recommended therapy for patients with type II diabetes is to reduce or reverse insulin resistance, improve metabolic control, and, ideally, do so without exacerbating hyperinsulinemia. The present invention comprises methods of treating these conditions by administering compositions that increase GSK-3β activity or increase the amount of GSK-3β to reduce hyperinsulinemia-associated vasculopathy.

The dosage of the compositions comprising the compound effecting GSK-3β will depend on the condition being treated, the particular compound, and other clinical factors such as weight and condition of the human or animal and the route of administration of the composition. It is to be understood that the present invention has application for both human and veterinary use. For oral administration to humans or animals, a dosage of between approximately 0.01 to 300 mg/kg/day, preferably between approximately 0.5 and 50 mg/kg/day, and most preferably between approximately 1 to 10 mg/kg/day, is generally sufficient.

The formulations include those suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tamports, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

As used herein, "effecting GSK-3β" includes inhibiting or stimulating the activity of GSK-3β protein, or increasing or decreasing the amount of GSK-3β protein. Compounds or compositions that cause these effects are referred to as effectors of GSK-3β.

Compositions comprising compounds that induce GSK-3β are useful for controlling TNF-induced as well as diabetic inflammation. Compositions with GSK-3β stimulating effects are useful as anti-inflammatory and anti-proliferative therapeutics. These selective activators of GSK-3β include small organic molecules, peptides, peptoids, or polynucleotides that act directly upon GSK-3β to modulate the enzymatic activity or to increase the biological stability of the enzyme. In addition, the selective activators of GSK-3β can be small organic molecules, peptides, peptoids, or polynucleotides that increase the biosynthesis of GSK-3β by increasing the transcription of the GSK-3β gene, increasing the biological stability of the GSK-3β mRNA or increasing the translation of GSK-3β mRNA into protein. Furthermore, the selective activators of GSK-3β can be small organic molecules, peptides, peptoids, or polynucleotides that block or decrease the effects of agents or proteins that inhibit the activity of GSK-3β.

The present invention also comprises methods and compositions for assays that are useful in identifying such selective activators or inhibitors of GSK-3β. These assays quickly and easily determine the activators that up-regulate and inhibitors that down-regulate the amount of GSK-3β and its activity. In general, such assays include, but are not limited to, promoter-based assays to identify effectors of GSK-3β; treating cells with GSK-3β inhibitors, including but not limited to insulin or lithium, then screening for compounds that alter the concentration of inflammatory cytokines in the media; treating cells with inflammatory molecules, and screening for compounds that are effectors of GSK-3β; assays for GSK-3β enzyme activity in recombinant, partially purified protein, or lysates from cells expressing GSK-3β in the presence or absence of compounds of interest. Measurements of GSK-3β include enzyme activity assays and quantitation of GSK-3β protein, using ELISA or Western blot determinations, or quantitation of GSK-3β RNA using RT_PCR, or Northern blots.

A preferred method of the present invention comprises the following. Cells are incubated with the compound to be tested, such compound being a potential effector of GSK-3β, in the presence or absence of an inflammatory molecule, such as a cytokine, preferably an inflammatory agent such as TNFα, oxidized LDL, Il-1β or AGE. The cells or supernatant are tested for a determinant of GSK-3β activity or expression. The measurement of the effects on GSK-3β indicates whether the suspected compound is an activator or suppressor of GSK-3β. For example, one set of endothelial cells are incubated with the compound to be tested alone, and one set of endothelial cells are incubated with the compound to be tested and TNFα. One or more determinants of GSK-3β activity or expression are measured, such as measuring Il-6, VCAM-1 or MCP-1 using an ELISA specific for each. Determinant of GSK-3β activity or expression as used herein includes any changes that are measurable and occur because the GSK-3β gene, mRNA, protein or activity level has been altered. For example, measurement of such determinants includes, but is not limited to, measurement of the amount of GSK-3β protein or mRNA present in cells or supernatants, measurement of changes in cellular factors due to changes in GSK-3β, such as measurement of IL-6, VCAM or MCP-1; and measurements in changes of expression of genomic or recombinant GSK-3β genes or promoters or proteins that effect expression. If the level of the determinant is decreased, then the suspected compound is an enhancer of GSK-3β and if the level of the determinant is increased, the suspected compound is an inhibitor of GSK-3β. In these assays, the cells may be pretreated by incubation with inflammatory agents such as AGE or TNFα, prior to addition of the compound being tested. Such assays can be modified for automation and high throughput screening. Additionally, effects of direct inhibition of GSK-3β can be confirmed by addition of known specific inhibitors of GSK-3β, such as lithium, insulin, or GSK-3β or oligonucleotide anti-sense prior to or at the step of incubation with the compound to be tested. Alternatively, determination of compounds effecting GSK-3β can be accomplished in the presence of known stimulators of GSK-3β. A preferred method comprises an assay wherein the compound being tested is incubated alone with cells and the compound is incubated with cells in the presence of a known stimulator of GSK-3β, such as VEGF. Alternatively, the cells may have been pre-incubated with the known stimulator prior to incubation with the compound being tested.

Another preferred method of identifying and determining compounds that are effectors of GSK-3β comprises measuring the GSK-3β enzymatic activity in lysates of cells that have been infected with a vector, preferably an adenoviral vector, containing the cDNA coding for GSK-3β. The enzymatic activity in such lysates are determined in the presence or absence of a compound to be tested, such compound being a potential effector of GSK-3β, and the enzymatic activity measured. The means for the measurement of enzymatic activity are several and known to those skilled in the art. A preferred method involves the measurement of the amount of phosphorylation of protein or peptide substrate containing the phosphorylation consensus sequence for GSK-3β. Alternatively, cells could also be transfected with a plasmid containing the GSK-3β cDNA, lysates of such transfected cells prepared, and the enzymatic activity measured. Other methods of the present invention comprise measuring the activity of purified or partially purified GSK-3β obtained from cells infected or transfected as described above, tissue extracts, bacteria expressing a recombinant form of GSK-3β, or any other system suitable for the expression of recombinant GSK-3β. The methods of expressing and purifying or partially purifying recombinant GSK-3β are known to those skilled in the art.

Both indirect and direct methods of measurement of changes in GSK-3β are contemplated by the present invention. The assay methods disclosed herein rely on indirect measurement of GSK-3β through measurement of determinants of GSK-3β activity or expression. Additionally, direct determination of the change in the amount of GSK-3β protein can be done using other immunological methods, such as Western blots, densitometric measurements or ELISA methods. Alternatively, the direct determination of the change in the amount of GSK-3β mRNA can be done using RT-PCR or Northern analysis methods which are known to one skilled in the art. Measurements are also directly made using lysates of cells, and purified or partially purified GSK-3β protein that is either a recombinant or natural form of the protein. The means for the measurement of enzymatic activity are known to those skilled in the art. A preferred method comprises the measurement of the amount of phosphorylation of protein or peptide substrate containing the phosphorylation consensus sequence for GSK-3β.

Another preferred method of identifying and determining compounds that are effectors of GSK-3β comprises identifying compounds that interact with the promoter regions of the GSK-3β gene, or interact and effect proteins that interact with the promoter region, and are important in the transcriptional regulation of GSK-3β expression. In general, the method comprises a vector comprising regulatory sequences of the GSK-3β gene and an indicator region controlled by the regulatory sequences, such as an enzyme, in a promoter-reporter construct. The protein product of the indicator region is referred to herein as a reporter enzyme or reporter protein. The regulatory region of the sequence of GSK-3β comprises a range of nucleotides from approximately −4000 to +953 wherein the transcription initiation site is +1, more preferably, from −2500 to +800, most preferably, from −1478 to +534 relative to the transcription initiation site.

Cells are transfected with the vector and then treated with compounds of interest. For example, the transfected cells are treated with a compound suspected of effecting the transcription of GSK-3β and the level of activity of the GSK-3β regulatory sequences are compared to the level of activity in cells that were not treated with the compound. In another example, the transfected cells are treated with inflammatory cytokines, such as TNFα, either before or with addition of a compound of interest. The level of activity of the GSK-3β regulatory sequences are determined by measuring the amount of the reporter protein or determining the activity of the reporter enzyme controlled by the regulatory sequences. An increase in the amount of the reporter protein or the reporter enzyme activity shows a stimulatory effect on GSK-3β, by positively effecting the promoter, whereas a decrease in the amount or the reporter protein or the reporter enzyme activity shows a negative effect on the promoter and thus, on GSK-3β.

Additionally, the present invention comprises methods and compositions for identifying selective inhibitors of GSK-3β protein or activity. These selective inhibitors of GSK-3β are small organic molecules, peptides, peptoids, or polynucleotides that act directly upon GSK-3β or the promoter region of GSK-3β to modulate the enzymatic activity or to decrease the biological stability of the enzyme. In addition, the selective inhibitors of GSK-3β can be small organic molecules, peptides, peptoids, or polynucleotides that decrease the biosynthesis of GSK-3β by decreasing the transcription of the GSK-3β gene, decreasing the biological stability of the GSK-3β mRNA or decreasing the translation of GSK-3β mRNA into protein. Furthermore, the selective inhibitors of GSK-3β can be small organic molecules, peptides, peptoids, or polynucleotides that block or decrease the effects of agents or proteins that increase the activity of GSK-3β.

This invention additionally comprises the use of gene therapy to control inflammatory responses. A more preferred method comprises the transfection of cells with a vector for the expression of GSK-3β.

The invention additionally comprises the use of gene therapy to control cell proliferation. A more preferred method comprises the transfection of cells, most preferably endothelial cells or smooth muscle cells, with a vector for the expression of GSK-3β.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

EXAMPLES

Example 1

RT-PCR of GSK-3β

Human aortic (HAEC) and microvascular (HMVEC) endothelial cells (Clonetics) were cultured and sub-cultured according to manufacturer in growth medium (Clonetics): basal medium containing hEGF, hydrocortisone, VEGF, HFGF-B (w/heparin), long R3-IGF-1, Ascorbic acid, gentamicin/amphotericin and 5% FBS. These cell were allowed to reach >90% confluency before subjected to experimental treatments. Glycated HSA (AGE) was from US Biologicals. Tumor necrosis factor α was from R&D Systems. HMVEC cells were treated with control medium or medium containing 10 ng/ml TNFα or 100 μg/ml glycated-HSA for 24 hrs. All treatments and controls were carried out in serum free media containing 0.2% albumin. Cells were collected into cold PBS using a cell scraper and used for RNA isolation.

Endothelial cells were incubated in media alone (control) or media containing TNFα (10 ng/ml) or AGE (100 μg/ml) for 8 hours. Poly (A) RNA was isolated and used as template for RT-PCR. Poly (A)+RNA was isolated from confluent cultures of HMVEC incubated under various conditions, using the Micropoly (A) pure kit (Ambion). RT-PCR with Superscript First-strand synthesis system (BRL) was performed according to the manufacture's instructions. Oligonucleotide primers for human GSK-3β gene amplification were; sense: SEQ. ID. NO: 1: TTCCTTTGGAATCTGC-CATC and antisense: SEQ. ID. NO. 2: GGGTCGGAAGACCTTAGTCC, representing a 406 bp region (from 519–925) in the coding sequence of GSK-3β (GSK-3β GenBank Accession No. L33801). 50 ng of poly (A) RNA and 0.5 μg of oligo (dT) primers were used for first-strand synthesis of cDNA in a reaction mixture also containing 10 mM dNTP and (with or without) the reverse transcriptase, SuperScript II RT. The reactions were terminated by heating the samples for 15 min at 70° C. Next, samples were pre-treated for 20 min at 37° C. with RNase H to remove RNA. PCR was carried out by using an initial denaturing step at 96° C. for 5 min, then cycle 35-times (or 25 times for quantitative RT-PCR) between 96° C. for 1 min, 58° C. for 45 sec, and 72° C. for 2 min. A final elongation step followed for 10 min at 72° C. Samples (10 μl) were analyzed on a 1% agarose gel and stained with ethidium bromide and visualized by UV Tran illuminator (UIVP).

FIG. 1 shows the inhibition of GSK-3β expression by TNFα and AGE. A 406 bp (shown by arrow) was observed in control endothelial cells only when reverse transcriptase (RT) was present. The intensity of this band was decreased when cells were either treated with TNFα or AGE.

Example 2

IL-6 ELISA

Inhibition of GSK-3β exacerbated TNFα-induced IL-6 production by endothelial cells. Two known inhibitors of GSK-3β, insulin and lithium were used. Lithium ions inhibit GSK-3β activity both in vitro and in intact cells (18, 19).

Human aortic (HAEC) and microvascular (HMVEC) endothelial cells (Clonetics) were cultured and subcultured according to manufacturer in growth medium (Clonetics): basal medium containing hEGF, hydrocortisone, VEGF, HFGF-B (w/heparin), long R3-IGF-1, Ascorbic acid, gentamicin/amphotericin and 5% FBS. These cell were allowed to reach >90% confluency before being subjected to experimental treatments. Glycated HSA (AGE) was from US Biologicals. Tumor necrosis factor α was from R&D Systems. Cells were incubated with 20 mM lithium (as LiCl or with 20 mM KCl as control) in the presence or absence of TNFα (10 ng/ml). Insulin (1 nM) was also used to inhibit GSK-3β.

HMVEC cells were treated with control medium or medium containing 10 ng/ml TNFα or 100 μg/ml glycated-HSA for 24 hrs. All treatments and controls were carried out in serum free media containing 0.2% albumin. Following treatment, cell media were collected and used for IL-6, MCP-1 ELISA and cells were used for VCAM-1 ELISA which was conducted in situ without lysis.

IL-6 ELISA was carried out using human IL-6 DuoSet ELISA development kit as described by manufacturer (R&D Systems). Mouse anti-human Il-6 was used as the capture antibody (2 μg/ml) and biotinylated goat anti-human IL-6 (200 ng/ml) was used as the detection antibody. Culture media was incubated with capture antibody (in 96 well) for 2 h at room temperature. Wells were washed three times with wash buffer (0.05% Tween-20 in phosphate-buffered saline (PBS) pH 7.4) followed by incubation with detection antibody for 2 h at room temperature. Following three washes, the wells were incubated with Streptavidin-HRP for 20 min. Color development was read at 450 nm in a microplate reader.

Figure 2:
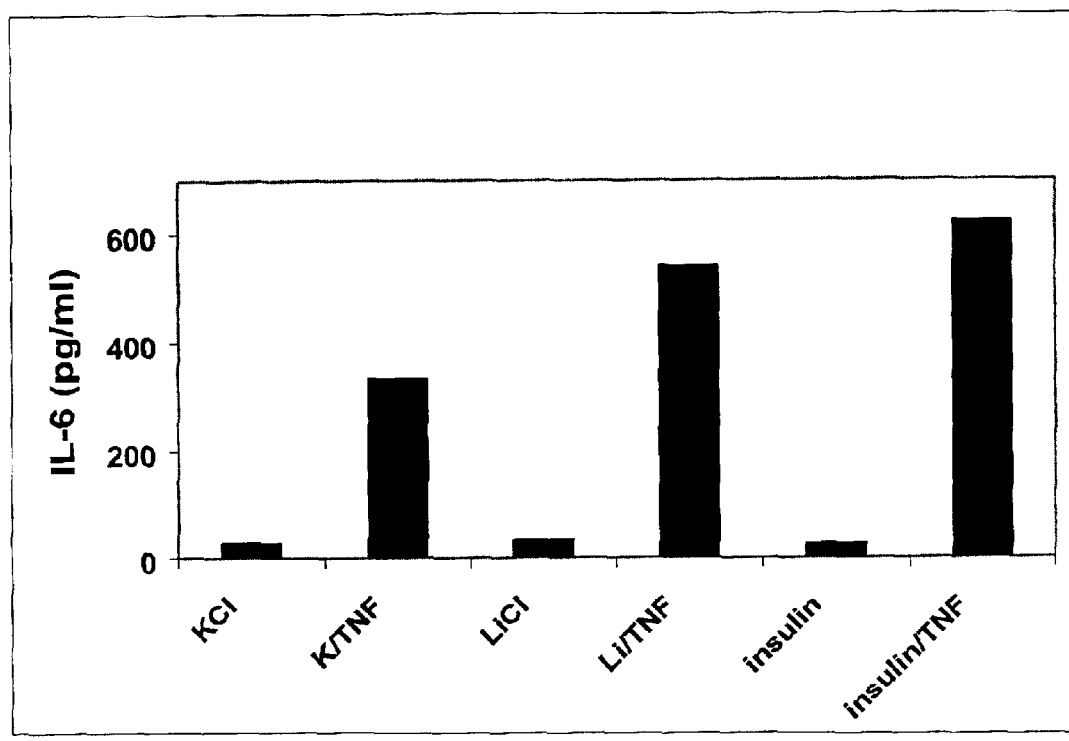
FIG. 2 is a graph showing endothelial production of IL-6.

As shown in FIG. 2, inhibition of GSK-3β exacerbated TNFα-induced IL-6 production. Endothelial cells were exposed to KCl (10 mM, as a control) or with TNFα (10 ng/ml); LiCl (10 mM) alone and with TNFα (10 ng/ml), insulin (1 nM) alone or with TNFα (10 ng/ml). Following incubation for 24 h, media were collected and assayed for IL-6 by ELISA. Plotted values are means of duplicate determinations. The standard deviation from the mean was ±10% of the mean value.

The effects of these agents on IL-6 secretion are shown in FIG. 2. Endothelial cells under basal conditions secreted about 25 pg/ml of IL-6. Incubation of endothelial cells with KCl, LiCl or insulin did not affect IL-6 secretion (28–34 pg/ml). TNFα induced greater than 10 fold increase in IL-6 secretion by endothelial cells. Although lithium and insulin treatments alone did not affect IL-6 secretion, when added with TNFα, they further increased IL-6 secretion by 60–90%. Specific inhibition of GSK-3β exacerbated TNFα effects. The lack of effect of lithium and insulin in the absence of TNFα showed GSK-3β acted by regulating the nuclear actions of NF-κB but did not induce its nuclear translocation.

Example 3

MCP-1 ELISA

Figure 4:
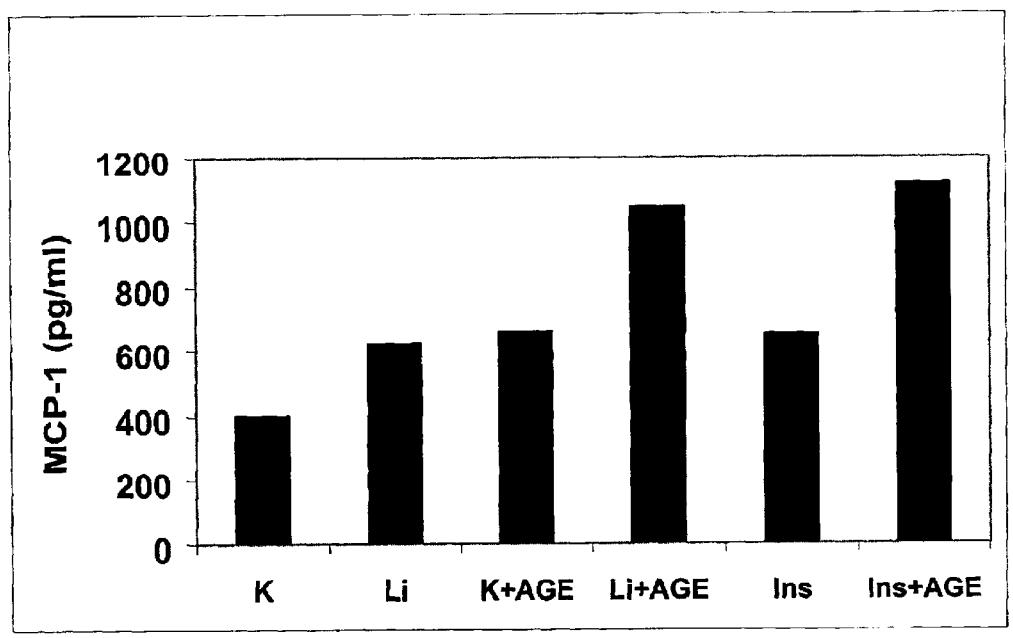
FIG. 4 is a graph showing the endothelial cell production of MCP-1.

This Example showed that GSK-3β exacerbated AGE-induced MCP-1 production by endothelial cells. Like TNFα, AGE treatment decreased the expression of GSK-3β in endothelial cells. AGE has been shown to induce MCP-1, another pro-inflammatory cytokine and glycated albumin positively correlates with MCP-1 in patients with diabetic nephropathy. The effects of AGE on endothelial MCP-1 are shown in FIG. 4. The cells were treated as described in Example 2, except for the use of AGE and not TNFα. Endothelial cells were exposed to KCl (10 mM, as control) or LiCl (10 mM), KCl (10 mM) and AGE (300 μg/ml), LiCl (10 mM) and AGE (300 μg/ml); insulin (1 nM); and insulin (1 nM) and AGE (300 μg/ml. Following incubation for 24 h, media were collected and assayed for MCP-1 by ELISA.

MCP-1 ELISA was carried out using Quantikine Human MCP-1 kit as described by manufacturer (R&D Systems). Mouse anti-human MCP-1 was used as the capture antibody and HRP-conjugated goat anti-human MCP-1 was used as the detection antibody. Culture media were incubated with capture antibody (in 96 well) for 2 h at room temperature. Wells were washed three times with wash buffer (0.05% Tween-20 in PBS followed by incubation with detection antibody for 2 h at room temperature. Color development was read at 450 nm in a microplate reader.

Endothelial cells when incubated with 10 mM KCl produced about 400 pg/ml MCP-1. Incubation with lithium alone or insulin alone increased MCP-1 secretion by about 50%. When added together, lithium and AGE increased MCP-1 by 2.6 fold, whereas insulin and AGE increased MCP-1 by approximately 2.8 fold, showing that inhibition of GSK-3β exacerbated AGE-induced inflammatory events.

FIG. 4 shows that inhibition of GSK-3β exacerbated AGE-induced MCP-1 production. Plotted values are means of duplicate determinations. The standard deviation from the mean was ±10% of the mean value.

Example 4

VCAM-1 ELISA

Inhibition of GSK-3β altered inflammation-related adhesion molecule expression. VCAM-1 is an endothelial adhesion molecule that facilitates monocyte infiltration into the blood vessel (3). Cells were treated as described in Example 2. Endothelial cells were exposed to KCl (10 mM, as a control) or with TNFα (10 ng/ml); LiCl (10 mM) alone and with TNFα (10 ng/ml), insulin (1 nM) alone or with TNFα (10 ng/ml). Following incubation for 24 h, media were collected and assayed for VCAM-1 by ELISA.

VCAM-1 ELISA was performed on monolayers of endothelial cells in 96 well plates. Wells were incubated with 100 μl of 1:1000 dilution of primary antibody (polyclonal goat anti-human VCAM-1 from R&D Systems) in medium containing 10% FBS. A rabbit anti-goat IgG-HRP was used as secondary antibody and ELISA was performed as described for MCP-1 above.

Figure 3:
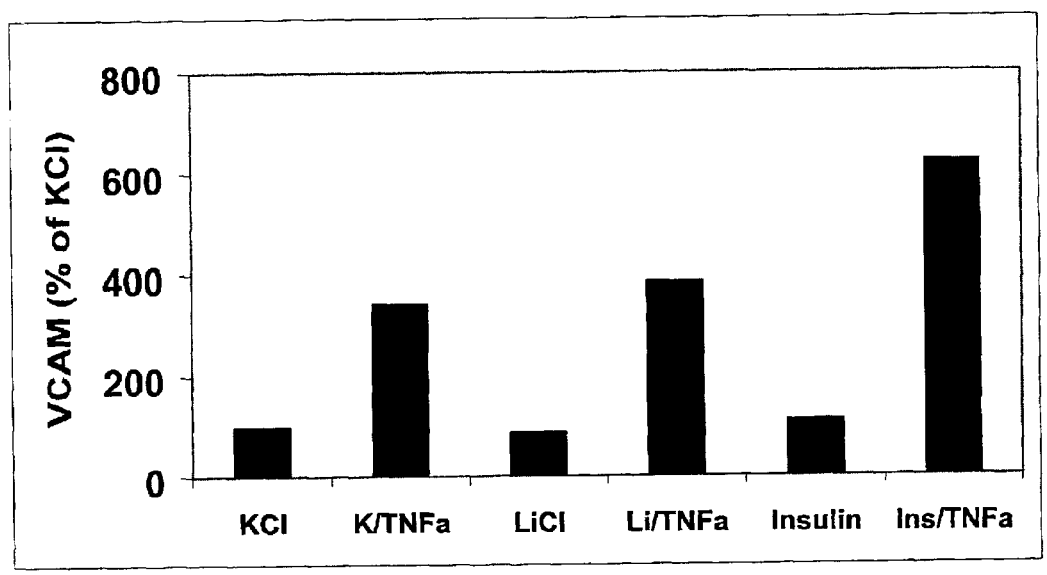
FIG. 3 is a graph showing the endothelial cell production of VCAM-1.

The effects of GSK-3β inhibition on VCAM-1 expression are shown in FIG. 3. Lithium and insulin did not significantly affect VCAM expression. TNFα increased VCAM-1 expression to 340% of basal levels. Addition of Li to TNFα further increased VCAM-1 expression (to 380%). Strikingly, TNFα when added together with insulin almost doubled the effect of TNFα alone on VCAM-1 expression showing that inhibition of GSK-3β is pro-inflammatory. Plotted values are means of duplicate determinations. The standard deviation from the mean was ±10% of the mean value.

Example 5

GSK-3β Expression

Figure 6:
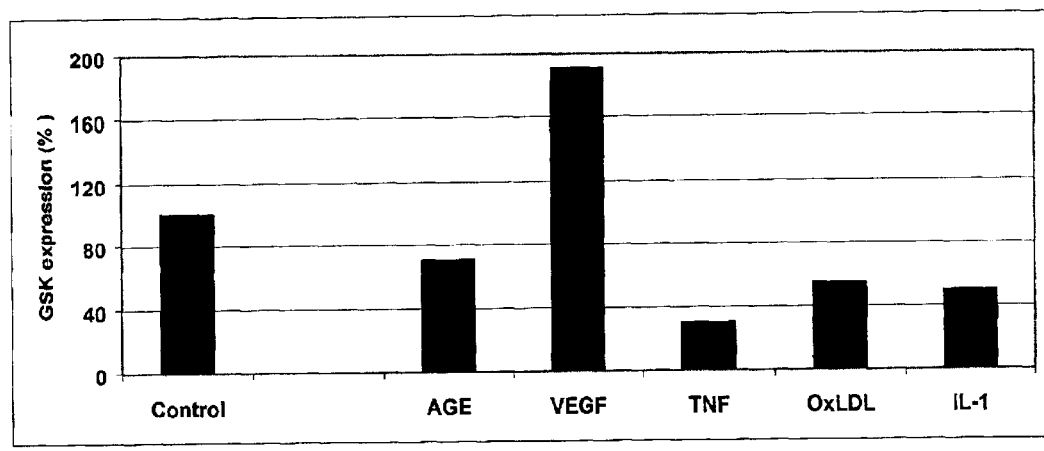
FIG. 6a is a graph of regulation of GSK-3β by inflammatory agents.
FIG. 6b is a photograph of western blot of GSK-3β expression in response to inflammatory agents.
Figure 6:
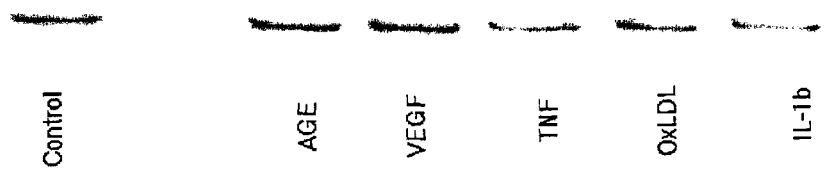

GSK-3β-immunoblotting analyses of endothelial cells treated with different inflammatory and non-inflammatory agents were performed. These data, western blotting and densitometric analysis of the bands, were plotted as shown in FIG. 6(a).

Cells were treated as taught in Examples 1 and 2. Endothelial cells were incubated with an agent for 24 hours. The inflammatory agents used were TNF-α, 10 ng/ml, glycated albumin (AGE, 300 μg/ml), oxidized LDL (100 μg/ml) and IL-1β (1 ng/ml); and a stimulatory agent, VEGF, (10 ng/ml). After incubation, the cells were washed, lysed and separated by polyacrylamide gel electrophoresis. Western blotting was performed, using antibody directed to GSK-3β, and detected.

GSK-3β expression was decreased by all the inflammatory agents tested in this study: TNF-α, 10 ng/ml, by 70%, glycated albumin (AGE, 300 μg/ml), oxidized LDL (100 μg/ml) and IL-1β (1 ng/ml) by 25–50%. Vascular endothelial growth factor (VEGF, 10 ng/ml) in contrast induced GSK-3β expression by almost 2 fold. Thus, these data show that GSK-3β expression is down regulated by inflammatory agents.

Example 6

Antisense Inhibition of GSK-3β

To rule out the possibility of non-GSK-3β mediated effects of lithium and insulin and to specifically address GSK-3β contribution to inhibition of inflammation, antisense oligonucleotides designed to block GSK-3β translation were used. Phosphorothioate-derivatives of the following oligonucleotides based on the sequence of GSK-3β were synthesized.

Sense: SEQ ID NO: 3 ATGTCAGGGCGGCCCAGAAC-CACCTC (ATG represents the start codon of GSK-3β).
Antisense: SEQ ID NO: 4 GAGGTGGTTCTGGGCCGC-CCTGACAT (complimentary to GSK-3β mRNA)

Endothelial cells, as grown in Example 1 and 2, were transfected with oligonucleotides using Cytofectin transfection reagent. Following 24 h transfection, the cells were incubated for 24 h with medium alone or medium containing 300 μg/ml glycated albumin (AGE) or medium containing 10 ng/ml TNF-α. IL-6 and MCP-1 were determined by ELISA, as shown in Examples 2 and 3.

Figure 7:
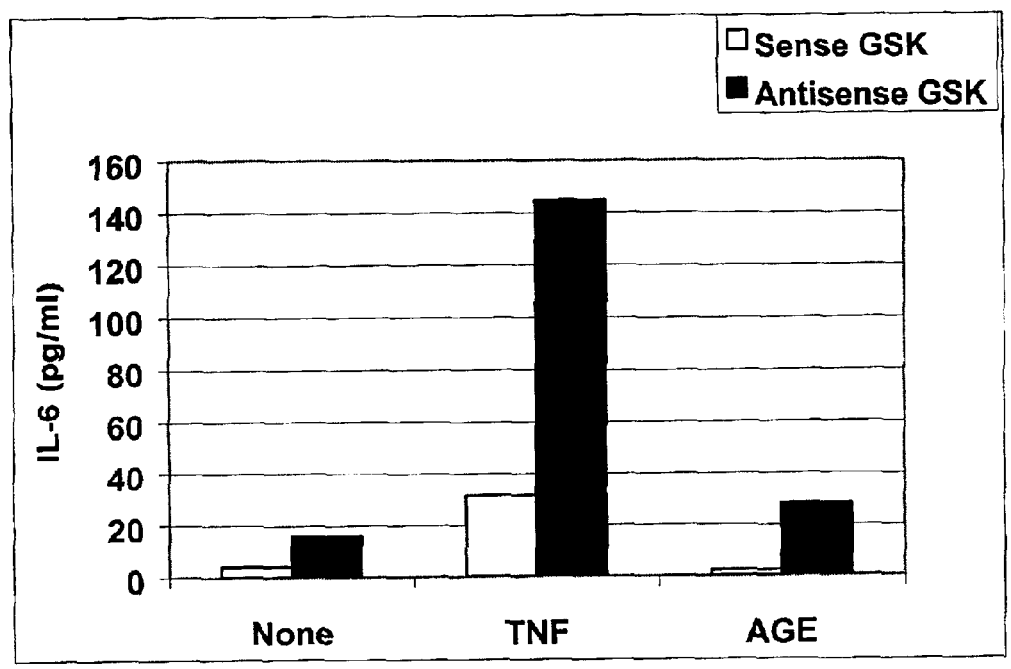
FIG. 7 is a graph of the effects on IL-6 secretion in sense and antisense oligonucleotide transfected cells.
Figure 8:
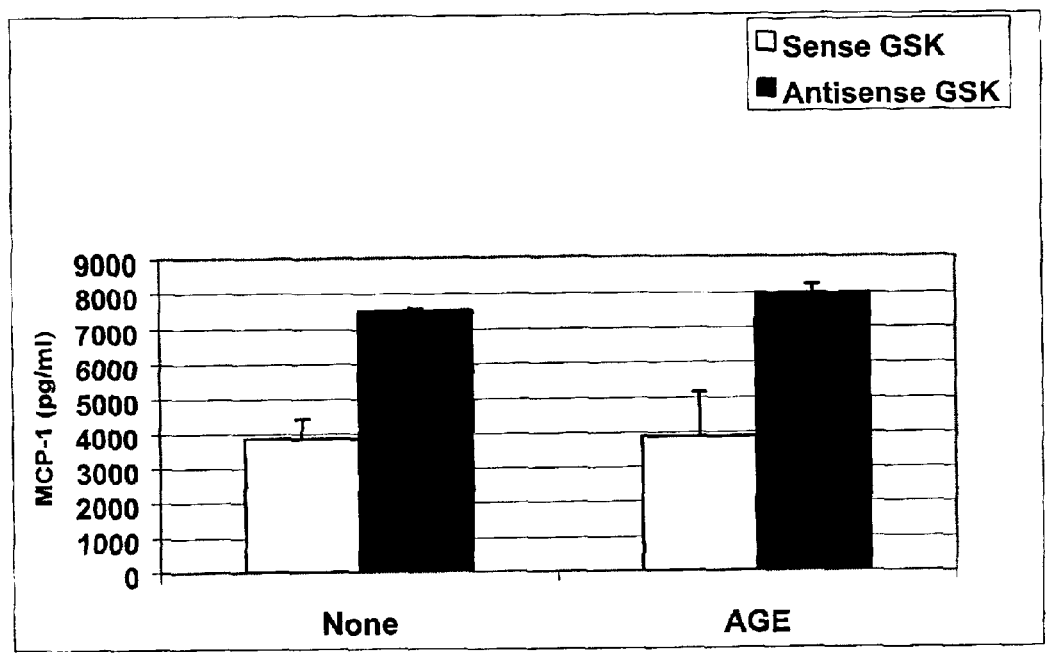
FIG. 8 is a graph of the effects on MCP-1 secretion in sense and antisense oligonucleotide transfected cells.

The effects of these treatments on IL-6 and MCP-1 secretion in sense and antisense oligonucleotide transfected cells are shown in FIGS. 7 and 8. Inhibition of GSK-3β led to 4–6 fold increase in IL-6 secretion compared to sense transfected cells. This increase was observed both in basal level IL-6 secretion and that induced by TNF-α and AGE. Inhibition of GSK-3β also resulted in induction of MCP-1 secretion by 2 fold. These data show that specific inhibition of GSK-3β exacerbates inflammatory response in endothelial cells.

Example 7

Overexpression of GSK-3β

Inhibition of GSK-3β led to increased inflammatory gene expression in endothelial cells. Overexpression of GSK-3β protein inhibited inducible inflammatory gene expression in endothelial cells. Full length GSK-3β cDNA was cloned into a retroviral vector pLIB. Empty vectors or vectors carrying alkaline phosphatase were used as controls. Retroviral particles carrying different genes were generated in HEK-293 cells. Endothelial cells were transduced with different vectors and 24 h following transduction, cells were either treated with medium or medium containing TNFα or AGE, as above. IL-6 and MCP-1 were determined by ELISA as described in Examples 2 and 3.

Figure 9:
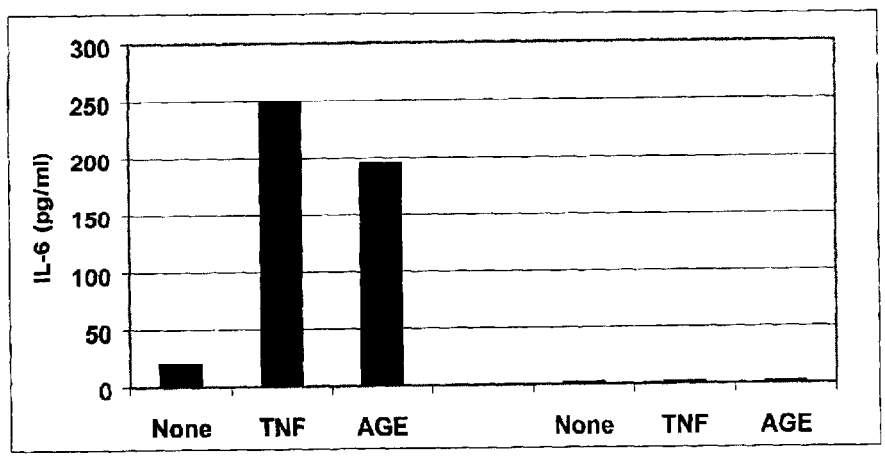
FIG. 9a is a graph of the effects of GSK-3β overexpression on IL-6.
FIG. 9b is a graph of the effects of GSK-3β overexpression on MCP-1.
FIG. 9c. is a photograph of Western Blot demonstrating overexpression of GSK-3β in cells transduced with GSK-3β vector.
Figure 9:
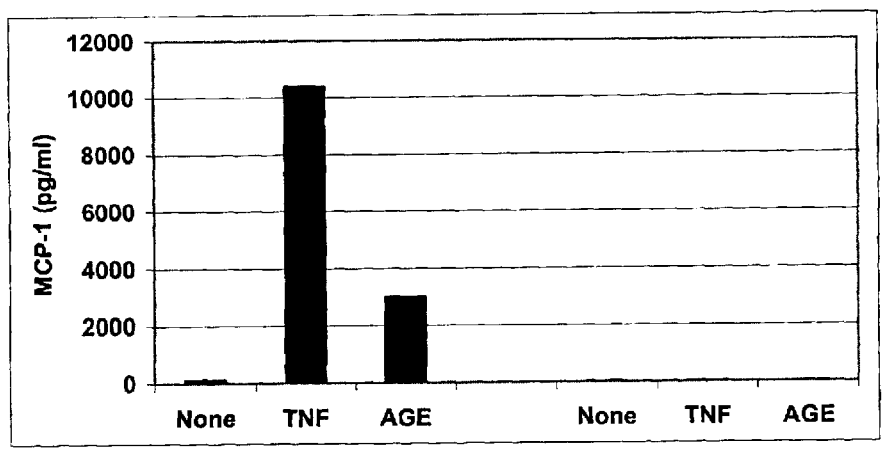
Figure 9:

The effects of GSK-3β overexpression are shown in FIG. 9. AGE and TNF induced IL-6 expression in endothelial cells transduced with control vector by 7 and 10 fold respectively (FIG. 9(a)). This induction was completely abrogated in endothelial cells transduced with GSK-3β carrying vector. Similar results were also found with MCP-1 induction. The ability of TNF and AGE to induce MCP-1 was completely abolished by GSK-3β overexpression (FIG. 9(b)). Western blot analysis of cells revealed overexpression of GSK-3β in cells transduced with GSK-3β vector (FIG. 9(c)). These data further confirm that GSK-3β is a potent anti-inflammatory molecule, and that induction of this protein inhibits inflammatory gene expression induced by inflammatory agents.

Example 8

Effects of GSK-3β on Smooth Muscle Cell Proliferation

Figure 10:
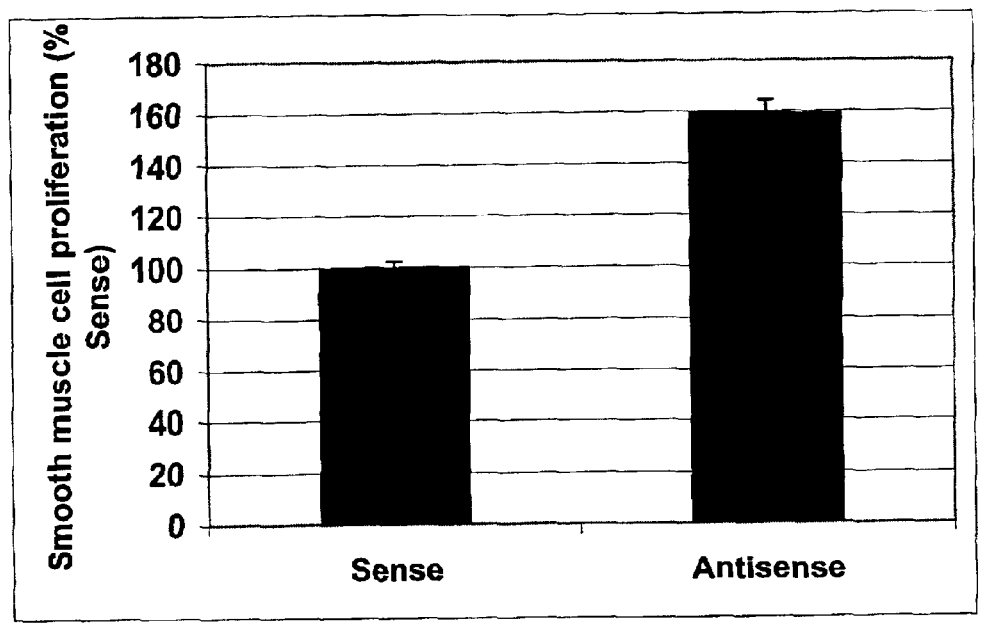
FIG. 10 is a graph of effects of GSK-3β on smooth muscle cell proliferation.

GSK-3β effects smooth muscle cell proliferation. The effects of GSK-3β inhibition on cell growth were tested using human aortic smooth muscle cells. Smooth muscle cells were transfected with either sense oligonucleotides or antisense-GSK-3β oligonucleotides, as described in Example 6, and cell growth was assessed for 48 h. These data are shown in FIG. 10. Inhibition of GSK-3β led to a 60% increase in smooth muscle cell proliferation, showing that GSK-3β is also anti-proliferative.

The Examples included herein demonstrated that GSK-3β mRNA was expressed in endothelial cells which are key modulators of the inflammatory response and that GSK-3β was transcriptionally regulated. Two different pro-inflammatory molecules TNFα and AGE decreased the expression of GSK-3β mRNA. The Examples also show that inhibition of GSK-3β potentiated TNFα/AGE ability to induce inflammatory response. Three different mediators of inflammation were induced in the presence of two different inhibitors of GSK-3β, insulin and Lithium. The Examples also demonstrated that GSK-3β had anti proliferative activity and inhibited smooth muscle cell proliferation.

Example 9

A promoter-reporter Construct

A ~2.1 kb GSK3β promoter (−1478 to +534, relative to transcription initiation site) was cloned from a human genomic library by PCR. The PCR product was sub-cloned into the T/A cloning vector pCR2.1-TOPO (Invitrogen). The GSK-3β promoter was released from pCR2.1-TOPO by restriction digestion with Kpn I and Xho I restriction digestion and ligated into same sites in the luciferase reporter vector pGL3-Basic (Promega), upstream of the luciferase gene. The resulting promoter-reporter construct was designated pGL3-GSK3B-1478/+534.

Example 10

Figure 11:
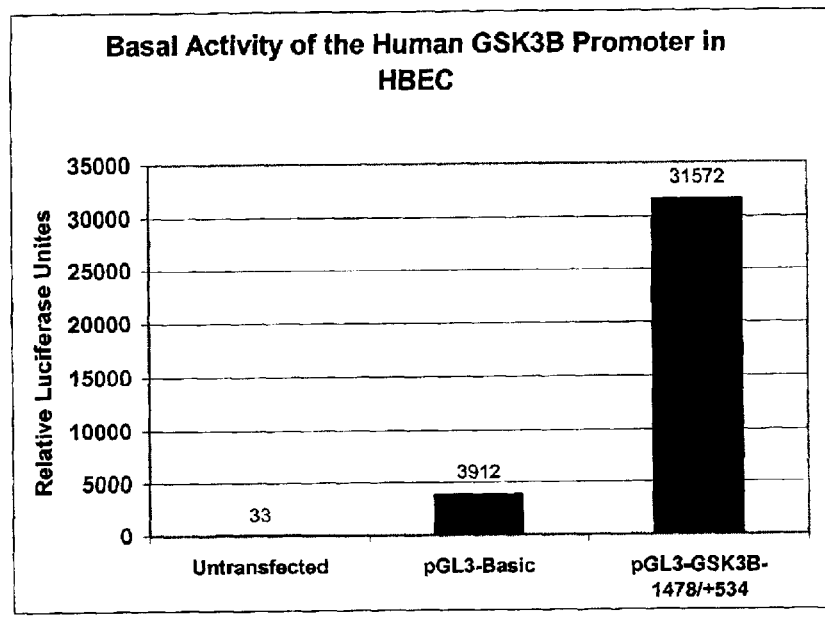
FIGS. 11 A and B are graphs showing luciferase activity in cells transfected with a GSK-3β promoter construct.
Figure 11:
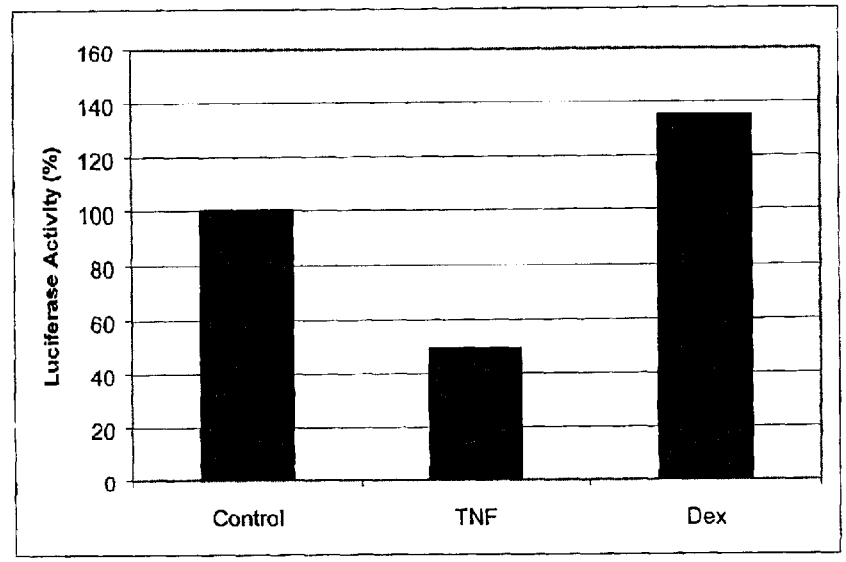

Transfection with a Promoter-reporter Construct pGL3-GSK3B−1478/+534 was transfected into bovine aortic endothelial cells (BAEC) by electroporation. Transfected cells were aliquoted into 96 well plates and allowed to recover in full media for 16–24 hours. For promoter regulation study, either control media, or media containing TNFα or dexamethasone (1 μM), were added to cells and incubated for 24–48 hours. Luciferase activity was measured in cell lysates using Bright-Glo Luciferase Assay System (Promega). Luciferase activity was significantly increased when transfected under the control of GSK-3β promoter (pGL3 GSK-3β) compared to luciferase expression in the absence of promoter (pGL3 basic) FIG. 11(a). The promoter activity was modulated by pro- and anti-inflammatory agents. Treatment with TNFα (10 ng/ml), a known pro-inflammatory agent, decreased GSK-3β promoter activity by greater than 50%. In contrast, dexamethasone, a known anti-inflammatory agent increased GSK-3β promoter activity by 35% FIG. 11(b). These data show that GSK-3β expression was regulated at transcriptional level and that agents that regulate GSK-3β expression can be identified using a promoter based approach.

All patents, patent applications, and scientific articles cited herein are incorporated in their entirety by reference.

As used herein, "a" or "an" can mean multiples. For example, "a cell" can mean at least one cell or more than one cell.

The following references are hereby incorporated by reference herein in their entirety.

References:
(1) Laight D W, Carrier M J, Anggard E E. Endothelial cell dysfunction and the pathogenesis of diabetic macroangiopathy. Diabetes Metab Res Rev. 15:274–82 (1999)
(2) Stehouwer C D, Lambert J, Donker A J, van Hinsbergh V W. Endothelial dysfunction and pathogenesis of diabetic angiopathy. Cardiovasc. Res.34:55–68 (1997).
(3) Welsh, G. I., Wilson, C. & Proud, C. G. GSK-3: a SHAGGY frog story. Trends Cell Biol. 6, 274–279 (1996).
(4) Lau K F, Miller C C, Anderton B H, Shaw P C. Expression analysis of glycogen synthase kinase-3 in human tissues. J. Pep. Res. 54(1):85–91 (1999).
(5) Cross, D. A., Alessi, D. R., Cohen, P., Andjelkovich, M. & Hemmings, B. A. Inhibition of glycogen synthase kinase-3 by insulin mediated by protein kinase B. Nature 378, 785–789 (1995)
(6) Sutherland C, Leighton I A, Cohen P. Inactivation of glycogen synthase kinase-3 beta by phosphorylation: new kinase connections in insulin and growth-factor signalling. Biochem J. 296:15–9 (1993).
(7) Beg, A. A. & Baltimore, D. An essential role for NF-κB in preventing TNF-[alpha]-induced cell death. Science 274, 782–784 (1996).
(8) Van Antwerp, D. J., Martin, S. J., Kafri, T., Green, D. R. & Verma, I. M. Suppression of TNF-[alpha]-induced apoptosis by NF-κB. Science 274, 787–789 (1996).
(9) Read, M. A., Whitley, M. Z., Williams, A. J., and Collins, T. NF-κB and IκB an inducible regulatory system in endothelial activation. J. Exp. Med. 179:503–512 (1994)
(10) Tracey, K. J., and A. Cerami. 1993. Tumor necrosis factor, other cytokines and disease. Annu. Rev. Cell Biol. 9:317.
(11) Green E A, Flavell R A. Tumor necrosis factor-alpha and the progression of diabetes in non-obese diabetic mice. Immunol. Rev. 169:11–22. (1999).
(12) Ceriello A. Hyperglycaemia: the bridge between non-enzymatic glycation and oxidative stress in the pathogenesis of diabetic complications. Diabetes Nutr. Metab. 12:42–6 (1999)
(13) Klein, P. S. & Melton, D. A. A molecular mechanism for the effect of lithium on development. Proc. Natl Acad. Sci. USA 93, 8455–8459 (1996).
(14) Stambolic, V., Ruel, L. & Woodgett, J. R. Lithium inhibits glycogen synthase kinase-3 activity and mimics wingless signalling in intact cells. Curr. Biol. 6, 1664–1668 (1996)
(15) Summers S A, Kao A W, Kohn A D, Backus G S, Roth R A, Pessin J E, Birnbaum M J. The role of glycogen synthase kinase 3beta in insulin-stimulated glucose metabolism. J Biol. Chem. 274:17934–40 (1999).
(16) Hanger D P, Hughes K, Woodgett J R, Brion J P, Anderton B H. Glycogen synthase kinase-3 induces Alzheimer's disease-like phosphorylation of tau: generation of paired helical filament epitopes and neuronal localization of the kinase. Neurosci Lett. 23;147:58–62. (1992)
(17) Lesort M, Jope R S, Johnson G V Insulin transiently increases tau phosphorylation: involvement of glycogen synthase kinase-3beta and Fyn tyrosine kinase. J Neurochem 72: 576–84 (1999)
(18) Ross S E, Erickson R L, Hemati N, MacDougald O A. Glycogen synthase kinase 3 is an insulin-regulated C/EBP alpha kinase. Mol. Cell Biol. 19:8433–41 (1999).
(19) Fiol C J, Williams J S, Chou C H, Wang Q M, Roach P J, Andrisani O M A secondary phosphorylation of CREB341 at Ser129 is required for the cAMP-mediated control of gene expression. A role for glycogen synthase kinase-3 in the control of gene expression. J. Biol. Chem. 269:32187–93 (1994)
(20) Wilson B E, Mochon E, Boxer L M. Induction of bcl-2 expression by phosphorylated CREB proteins during B-cell activation and rescue from apoptosis. Mol Cell Biol. 16:5546–56 (1996)
Badrichani A Z, Stroka D M, Bilbao G, Curiel D T, Bach F H, Ferran C. Bcl-2 and Bcl-XL serve an anti-inflammatory function in endothelial cells through inhibition of NF-kappaB. J Clin. Invest. 103:543–53 (1999).

---

What is claimed is:

1. A method for detecting a composition that effects the activity or expression of glycogen synthase kinase 3 beta (GSK-3β), comprising,
   a) adding an inflammatory molecule to a first cell culture and a second cell culture, wherein the first cell culture and the second cell culture contain the same type of cells;
   b) adding a composition comprising a test compound suspected of effecting the activity or expression of GSK-3β to the first cell culture;
   c) measuring the amount of a determinant of GSK-3β in the first cell culture and the second cell culture, wherein the determinant is a cellular factor which is vascular cell adhesion molecule 1 (VCAM-1), monocyte chemoattractant protein-1 (MCP-1), interleukin-6 (IL-6), interferon-inducible protein (IP-10), monokine induced by IFN-γ (MIG), or interferon-inducible T-cell α chemoattractant (1-TAC); and
   d) comparing the amount of the determinant of GSK-3β in the first cell culture to the amount of determinant in the second cell culture, wherein a difference between the amount of determinant in the first cell culture and the amount of determinant in the second cell culture indicates that the composition effects the activity or expression of GSK-3β.

2. The method of claim 1, wherein the test compound is a small organic molecule.

3. The method of claim 1, wherein the inflammatory molecule is a cytokine, an advanced glycation end product (AGE), or an oxidized low density lipoprotein (oxidized LDL).

4. The method of claim 3, wherein the cytokine is tumor necrosis factor α (TNFα) or interleukin 1β (IL-1β).

5. A method for detecting a composition that effects the expression of glycogen synthase kinase 3 beta (GSK-3β), comprising,
   a) adding an inflammatory molecule to a first cell culture and a second cell culture, wherein the first cell culture and the second cell culture contain the same type of cells;
   b) adding a composition comprising a test compound suspected of effecting the expression of GSK-3β to the first cell culture;
   c) measuring the amount of a determinant of GSK-3β in the first cell culture and the second cell culture, wherein the determinant is GSK-3β protein or GSK-3β mRNA; and
   d) comparing the amount of determinant of GSK-3β in the first cell culture to the amount of determinant in the second cell culture, wherein a difference between the amount of determinant in the first cell culture and the amount of determinant in the second cell culture indicates that the composition effects the expression of GSK-3β.

6. A method for detecting a composition that effects the activity or expression of glycogen synthase kinase 3 beta (GSK-3β), comprising,
   a) adding an inflammatory molecule to a first cell culture and a second cell culture, wherein the first cell culture and the second cell culture contain the same type of cells;
   b) adding a composition comprising a test compound suspected of effecting the activity or expression of GSK-3β to the first cell culture;
   c) measuring the amount of GSK-3β enzymatic activity in the first cell culture and the second cell culture; and
   d) comparing the amount of GSK-3β enzymatic activity in the first cell culture to the amount of GSK-3β enzymatic activity in the second cell culture, wherein a difference between the amount of determinant in the first cell culture and the amount of determinant in the second cell culture indicates that the composition effects the activity or expression of GSK-3β.

7. A method for detecting a composition that effects the activity or expression of GSK-3β, comprising,
   a) adding an inflammatory molecule to a first cell culture and a second cell culture, wherein the first cell culture and the second cell culture contain the same type of cells;
   b) adding a composition comprising a test compound suspected of effecting the activity or expression of GSK-3β to the first cell culture;
   c) adding a known effector of GSK-3β activity or expression to the first cell culture and the second cell culture;
   d) measuring the amount of a determinant of GSK-3β in the first cell culture and the second cell culture, wherein the determinant is a cellular factor which is vascular cell adhesion molecule 1 (VCAM-1), monocyte chemoattractant protein-1 (MCP-1), interleukin-6 (IL-6), interferon-inducible protein (IP-10), monokine induced by IFN-γ (MIG), or interferon-inducible T-cell α chemoattractant (I-TAG); and e) comparing the amount of determinant of GSK-3β in the first cell culture to the amount of determinant in the second cell culture, wherein a difference between the amount of determinant in the first cell culture and the amount of determinant in the second cell culture indicates that the composition effects the activity or expression of GSK-3β.

8. The method of claim 7, wherein the known effector of GSK-3β is an inhibitor of GSK-3β activity or expression.

9. The method of claim 8, wherein the inhibitor of GSK-3β is lithium or insulin.

10. The method of claim 7, wherein the known effector of GSK-3β is a stimulator of GSK-3β activity or expression.

11. The method of claim 10, wherein the stimulator is vascular endothelial growth factor (VEGF).

12. The method of claim 7, wherein the test compound is a small organic molecule.

13. The method of claim 7, wherein the inflammatory molecule is a cytokine, an AGE, or an oxidized LDL.

14. The method of claim 13, wherein the cytokine is TNFα or IL-1β.

15. A method for detecting a composition that effects the expression of GSK-3β comprising, a) adding an inflammatory molecule to a first cell culture and a second cell culture, wherein the first cell culture and the second cell culture contain the same type of cells;

b) adding a composition comprising a test compound suspected of effecting the expression of GSK-3β to the first cell culture;

c) adding a known effector of GSK-3β expression to the first cell culture and the second cell culture;

d) measuring the amount of a determinant of GSK-3β in the first cell culture and the second cell culture, wherein the determinant is GSK-3β protein or GSK-3β mRNA; and e) comparing the amount of determinant of GSK-3β in the first cell culture to the amount of determinant in the second cell culture, wherein a difference between the amount of determinant in the first cell culture and the amount of determinant in the second cell culture indicates that the composition effects the expression of GSK-3β.

16. A method for detecting a composition that effects the activity or expression of GSK-3β, comprising, a) adding an inflammatory molecule to a first cell culture and a second cell culture, wherein the first cell culture and the second cell culture contain the same type of cells;

b) adding a composition comprising a test compound suspected of effecting the activity or expression of GSK-3β to the first cell culture;

c) adding a known effector of GSK-3β activity or expression to the first cell culture and the second cell culture;

d) measuring the amount of GSK-3β enzymatic activity in the first cell culture and the second cell culture; and e) comparing the amount of GSK-3β enzymatic activity in the first cell culture to the amount of GSK-3β enzymatic activity in the second cell culture, wherein a difference between the amount of determinant in the first cell culture and the amount of determinant in the second cell culture indicates that the composition effects the activity or expression of GSK-3β.

17. A method for detecting a composition that effects the expression of GSK-3β comprising, a) transfection a first cell culture and a second cell culture with a DNA construct having promoter regulatory elements of the GSK-3β gene linked to a reporter gene, wherein the first and second set of cells are the same type of cells;

b) adding a composition suspected of effecting the expression of GSK-3β to the first cell culture;

c) measuring the amount of a determinant of the reporter gene in the first cell culture and the second cell culture, wherein the determinant is a reporter protein; and d) comparing the amount of the determinant in the first cell culture to the amount of determinant in the second cell culture, wherein a difference between the amount of determinant in the first cell culture and the amount of determinant in the second cell culture indicates that the composition effects the expression of GSK-3β.

18. The method of claim 17, further comprising adding an inflammatory molecule to the transfected cells prior to adding the composition suspected of effecting GSK-3β expression.

19. The method of claim 17, further comprising adding an inflammatory molecule when adding the composition suspected of effecting GSK-3β expression to the transfected cells.

20. The method of claim 17, further comprising adding a known effector of GSK-3β expression after adding the composition suspected of effecting GSK-3β expression to the cells.

21. The method of claim 20, wherein the known effector of GSK-3β expression is an inhibitor of GSK-3β expression.

22. The method of claim 21, wherein the inhibitor of GSK-3β expression is insulin.

23. The method of claim 17, wherein the known effector of GSK-3β expression is a stimulator of GSK-3β expression.

24. The method of claim 23, wherein the stimulator is VEGF.

25. The method of claim 17, wherein the test compound is a small organic molecule.

26. The method of claim 17, wherein the inflammatory molecule is a cytokine, an AGE, or an oxidized LDL.

27. The method of claim 26, wherein the cytokine is TNFα or IL-1β.

* * * * *